United States Patent
Kim et al.

(10) Patent No.: US 9,223,012 B2
(45) Date of Patent: Dec. 29, 2015

(54) ULTRASOUND IMAGE ENHANCEMENT BASED ON ENTROPY INFORMATION

(75) Inventors: Chul An Kim, Seoul (KR); Han Woo Lee, Seoul (KR)

(73) Assignee: Samsung Medison Co., Ltd., Kangwon-Do (KR)

( * ) Notice: Subject to any disclaimer, the term of this patent is extended or adjusted under 35 U.S.C. 154(b) by 142 days.

(21) Appl. No.: 13/109,416

(22) Filed: May 17, 2011

(65) Prior Publication Data

US 2012/0123265 A1 May 17, 2012

(30) Foreign Application Priority Data

Nov. 17, 2010 (KR) .................. 10-2010-0114332

(51) Int. Cl.
| | |
|---|---|
| A61B 8/00 | (2006.01) |
| G01S 7/52 | (2006.01) |
| A61B 8/08 | (2006.01) |
| G06T 5/00 | (2006.01) |
| G06T 5/50 | (2006.01) |

(52) U.S. Cl.
CPC ............. G01S 7/52046 (2013.01); A61B 8/488 (2013.01); A61B 8/52 (2013.01); A61B 8/5269 (2013.01); G01S 7/5205 (2013.01); G01S 7/52077 (2013.01); G06T 5/002 (2013.01); G06T 5/50 (2013.01); *G06T 2207/10132* (2013.01); *G06T 2207/20008* (2013.01); *G06T 2207/30004* (2013.01)

(58) Field of Classification Search
CPC .............. G01S 7/52046; G01S 7/5205; G01S 7/52077; G06T 2207/10132; G06T 2207/20008; G06T 2207/30004; G06T 5/002; G06T 5/50

USPC .......................................................... 600/443
See application file for complete search history.

(56) References Cited

U.S. PATENT DOCUMENTS 5,495,846 A * 3/1996 Uehara et al. ................. 600/443
5,579,358 A * 11/1996 Lin ................................ 378/4

(Continued)

FOREIGN PATENT DOCUMENTS

| EP | 0 430 094 | 11/1990 |
|---|---|---|
| JP | 03-234247 | 10/1991 |

(Continued)

OTHER PUBLICATIONS

Yan C, Sang N, Zhang T. Local entropy-based transition region extraction and thresholding. Pattern Recognition Letters 24: 2935-2941. 2003.*

(Continued)

*Primary Examiner* — Jonathan Cwern
*Assistant Examiner* — Amelie R Gillman
(74) *Attorney, Agent, or Firm* — McDermott Will & Emery LLP

(57) ABSTRACT

Embodiments for enhancing an image quality of an ultrasound image based on entropy information in an ultrasound system are disclosed. In one embodiment, an ultrasound data acquisition unit acquires multiple ultrasound data, and a processing unit forms entropy information based on the multiple ultrasound data and adaptively perform data processing for image enhancement upon the multiple ultrasound data based on the entropy information. The processing unit forms multiple ultrasound images based on the multiple ultrasound data with the data processing performed.

6 Claims, 4 Drawing Sheets

(56) References Cited

U.S. PATENT DOCUMENTS

| | | | |
|---|---|---|---|
| 6,154,560 A * | 11/2000 | Cothren et al. | 382/128 |
| 6,262,749 B1 * | 7/2001 | Finger et al. | 345/564 |
| 6,785,570 B2 * | 8/2004 | Nir | 600/407 |
| 2007/0025603 A1 * | 2/2007 | Dewaele et al. | 382/128 |
| 2007/0160286 A1 * | 7/2007 | Haque | 382/164 |
| 2008/0119732 A1 * | 5/2008 | Hiltawsky et al. | 600/438 |
| 2008/0260229 A1 * | 10/2008 | Mashiach | 382/131 |
| 2009/0131787 A1 | 5/2009 | Lee et al. | |
| 2010/0246884 A1 * | 9/2010 | Chen et al. | 382/103 |

FOREIGN PATENT DOCUMENTS

| | | |
|---|---|---|
| JP | 2002-163635 | 6/2002 |
| KR | 10-1991-0007874 | 10/1991 |
| KR | 10-2009-0052074 | 5/2009 |

OTHER PUBLICATIONS

Ming-Yu Liu; Tuzel, O.; Ramalingam, S.; Chellappa, R., "Entropy rate superpixel segmentation," Computer Vision and Pattern Recognition (CVPR), 2011 IEEE Conference on , vol., No., pp. 2097,2104, Jun. 20-25, 2011.*

Nillesen et al. Three Dimensional Segmentation of the Heart Muscle using Image Statistics. Proc. SPIE 6147, Medical Imaging 2006: Ultrasonic Imaging and Signal Processing, 61470N (Mar. 16, 2006).*

Noble. Ultrasound Image Segmentation: A Survey. IEEE Trans on Medical Imaging, vol. 25 No. 8, pp. 987-1010, Aug. 2006.*

Tay, P.C.; Acton, S.T.; Hossack, J.A., "A stochastic approach to ultrasound despeckling," Biomedical Imaging: Nano to Macro, 2006. 3rd IEEE International Symposium on , vol., No., pp. 221,224, Apr. 6-9, 2006.*

Yang, P.; Basir, O.A, "Adaptive weighted median filter using local entropy for ultrasonic image denoising," Image and Signal Processing and Analysis, 2003. ISPA 2003. Proceedings of the 3rd International Symposium on , vol. 2, No., pp. 799,803 vol. 2, Sep. 18-20, 2003.*

Xin-Yu Zhang; Lan Ge; Tian-Fu Wang, "Entropy-Based Local Histogram Equalization for Medical Ultrasound Image Enhancement," Bioinformatics and Biomedical Engineering, 2008. ICBBE 2008. The 2nd International Conference on, vol., No., pp. 2427,2429, May 16-18, 2008.*

* cited by examiner

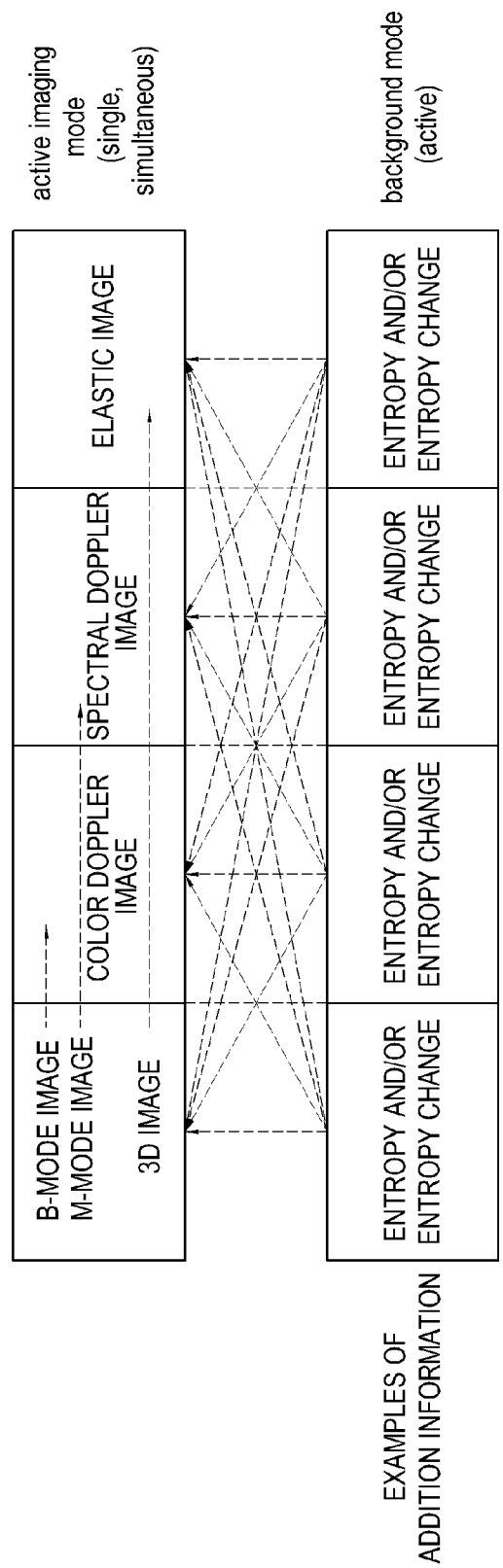

US 9,223,012 B2

ULTRASOUND IMAGE ENHANCEMENT BASED ON ENTROPY INFORMATION

CROSS-REFERENCE TO RELATED APPLICATIONS

The present application claims priority from Korean Patent Application No. 10-2010-0114332 filed on Nov. 17, 2010, the entire subject matter of which is incorporated herein by reference.

TECHNICAL FIELD

The present disclosure generally relates to ultrasound image, and more particularly to ultrasound image enhancement based on entropy information in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

The ultrasound system transmits ultrasound signals to a target object and receives ultrasound echoes reflected from the target object to thereby form an ultrasound image. Recently, a variety of image processing has been adopted in the ultrasound system to enhance an image quality of the ultrasound image.

Meanwhile, when a scan circumstance is rapidly changed in the target object (e.g., a contacting change of an ultrasound probe from air to a surface of the target object and vice versa), characteristics of input signals are also suddenly changed, which makes the ultrasound image degraded. Thus, it is required to adaptively enhance the image quality of the ultrasound image.

SUMMARY

Embodiments for enhancing an ultrasound image based on entropy information in an ultrasound system are disclosed herein. In one embodiment, by way of non-limiting example, an ultrasound system comprises: an ultrasound data acquisition unit configured to perform a transmit/receive operation including transmitting ultrasound signals to a target object and receiving ultrasound echoes reflected from the target object to thereby acquire multiple ultrasound data; and a processing unit configured to form entropy information based on the multiple ultrasound data and to adaptively perform data processing for image enhancement upon the multiple ultrasound data based on the entropy information, the processing unit being further configured to form multiple ultrasound images based on the multiple ultrasound data with the data processing performed.

In another embodiment, an ultrasound system comprises: an ultrasound data acquisition unit configured to perform a transmit/receive operation including transmitting ultrasound signals to a target object and receiving ultrasound echoes reflected from the target object to thereby acquire multiple ultrasound data; and a processing unit configured to form entropy information based on the multiple ultrasound data and to form multiple ultrasound images based on the multiple ultrasound data, the processing unit being further configured to adaptively perform image processing for image enhancement upon the multiple ultrasound image based on the entropy information.

In further another embodiment, a method of enhancing an image quality of an ultrasound images, comprises: a) performing a transmit/receive operation including transmitting ultrasound signals to a target object and receiving ultrasound echoes reflected from the target object to thereby acquire multiple ultrasound data; b) forming entropy information based on the multiple ultrasound data; c) adaptively performing data processing for image enhancement upon the multiple ultrasound data based on the entropy information; and d) forming multiple ultrasound images based on the multiple ultrasound data with the data processing performed.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 5 is a diagram showing background addition information (i.e., entropy information and/or entropy change information) for adaptive ultrasound image enhancement.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
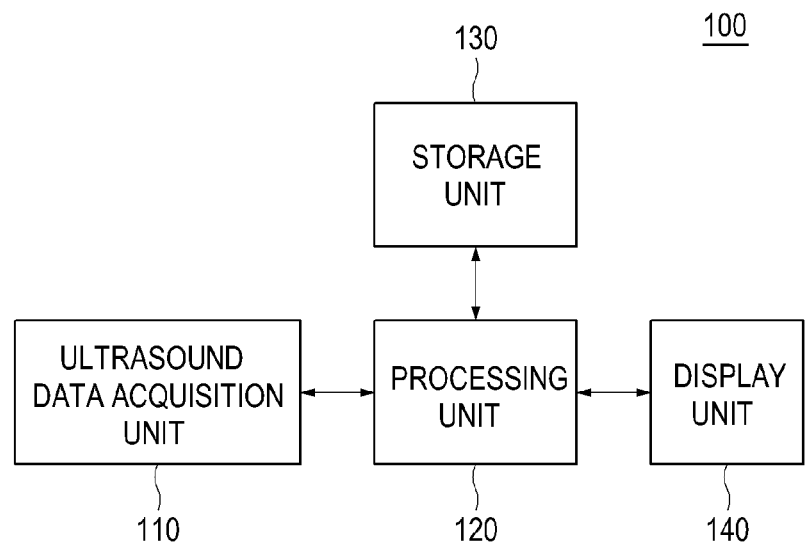
FIG. 1 is a block diagram showing an illustrative embodiment of an ultrasound system.

Referring to FIG. 1, an ultrasound system constructed in accordance with one embodiment is shown. The ultrasound system 100 may include an ultrasound data acquisition unit 110, a processing unit 120, a storage unit 130 and a display unit 140.

The ultrasound data acquisition unit 110 may be configured to transmit ultrasound beams to a target object and receive ultrasound echoes reflected from the target object to thereby form ultrasound data representative of the target object. An operation of the ultrasound acquisition unit 110 will be described in detail by referring to FIG. 2.

Figure 2:
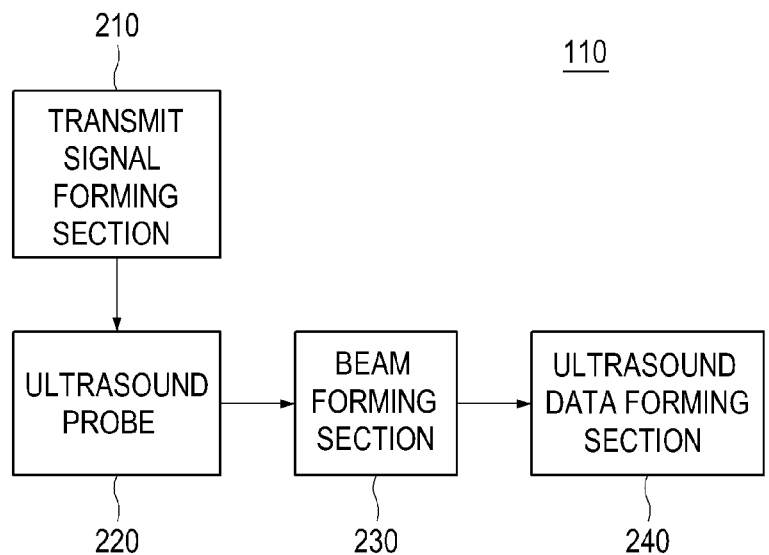
FIG. 2 is a block diagram showing an illustrative embodiment of an ultrasound data acquisition unit.

FIG. 2 is a block diagram showing an illustrative embodiment of the ultrasound data acquisition unit 110. Referring to FIG. 2, the ultrasound data acquisition unit 110 may include a transmit signal forming section 210. The transmit signal forming section 210 may generate a plurality of transmit signals. The transmit signal forming section 210 may form a transmit pattern of the transmit signals according to image modes such as a brightness mode, a color Doppler mode, a spectral Doppler mode and the like. In one embodiment, the transmit pattern of the transmit signals may include a first transmit pattern for the brightness mode. In another embodiment, the transmit pattern of the transmit signals may include a second transmit pattern for the brightness mode and a third transmit pattern for the color Doppler mode. In such a case, the second transmit pattern and the third transmit pattern may be repeatedly formed in a sequential manner. Further, in another embodiment, the transmit patter of the transmit signals may include a fourth transmit pattern for the brightness mode and a fifth transmit pattern for the spectral Doppler mode. In such a case, the fourth transmit pattern and the fifth transmit pattern may be repeatedly formed in a sequential manner.

The ultrasound data acquisition unit 120 may further include an ultrasound probe 220, which is coupled to the transmit signal forming section 210. The ultrasound probe 220 may include an array transducer containing a plurality of transducer elements for reciprocal conversion between electric signals and ultrasound signals. The ultrasound probe 220 may be configured to transmit ultrasound signals in response to the transmit signals. The ultrasound signals may be focused along scan lines based on the transmit patterns of the transmit signals, which are applied to the array transducer. In one embodiment, the transmitted ultrasound signals may include first ultrasound signals based on the first transmit pattern of the transmit signals. In another embodiment, the transmitted ultrasound signals may include second ultrasound signals based on the second transmit pattern of the transmit signals and third ultrasound signals based on the third transmit pattern of the transmit signals. Further, in another embodiment, the transmitted ultrasound signals may include fourth ultrasound signals based on the fourth transmit pattern of the transmit signals and fifth ultrasound signals based on the fifth transmit pattern of the transmit signals.

The ultrasound probe 220 may be further configured to receive ultrasound echoes reflected from the target object to thereby output receive signals. In one embodiment, the receive signals may include first to fifth receive signals associated with the first to fifth ultrasound signals according to the respective embodiments. The ultrasound probe 220 may include a convex probe, a linear probe, a three-dimensional mechanical probe and the like.

The ultrasound data acquisition unit 120 may further include a beam forming section 230, which is coupled to the ultrasound probe 220. The beam forming section 230 may be configured to digitize the receive signals into digital signals. The beam forming section 230 may be configured to apply delays to the digital signals in consideration of distances between the elements of the ultrasound probe 220 and focal points. The beam forming section 230 may further sum the delayed digital signals to form receive-focused signals. In one embodiment, the beam forming section 230 may form first receive-focused signals based on the first receive signals. In another embodiment, the beam forming section 230 may form second receive-focused signals based on the second receive signals and third receive-focused signals based on the third receive signals. Further, in another embodiment, the beam forming section 230 may form fourth receive-focused signals based on the fourth receive signals and fifth receive-focused signals based on the fifth receive signals.

The ultrasound data acquisition unit 120 may further include an ultrasound data forming section 240, which is coupled to the beam forming section 230. The ultrasound data forming section 240 may be configured to form ultrasound data based on the receive-focused signals. The ultrasound data forming section 240 may be further configured to perform a variety of signal processing, e.g., gain adjustment, upon the receive-focused signals for ultrasound data acquisition.

In one embodiment, the ultrasound data forming section 240 may form first ultrasound data corresponding to a plurality of B-mode images based on the first receive-focused signals. The first ultrasound data may include radio frequency (RF) data, although it is not limited thereto.

In another embodiment, the ultrasound data forming section 240 may form second ultrasound data corresponding to a plurality of B-mode images based on the second receive-focused signals. The second ultrasound data may be RF data, although it is not limited thereto. The ultrasound data forming section 240 may form third ultrasound data corresponding to a plurality of color Doppler images. The third ultrasound data may include in-phase/quadrature (IQ) data, although the third ultrasound data may not be limited thereto.

Further, in another embodiment, the ultrasound data forming section 240 may form fourth ultrasound data corresponding to a plurality of B-mode images based on the fourth receive-focused signals. The fourth ultrasound data may be RF data, although it is not limited thereto. The ultrasound data forming section 240 may form fifth ultrasound data corresponding to a plurality of spectral Doppler images. The fifth ultrasound data may include in-phase/quadrature (IQ) data, although the fifth ultrasound data may not be limited thereto.

Referring to FIG. 1, the processing unit 120, which is coupled to the ultrasound data acquisition unit 110, may be embodied with at least one of a central processing unit, a microprocessor, a graphic processing unit and the like. However, the processing unit 120 may not be limited thereto.

Figure 3:
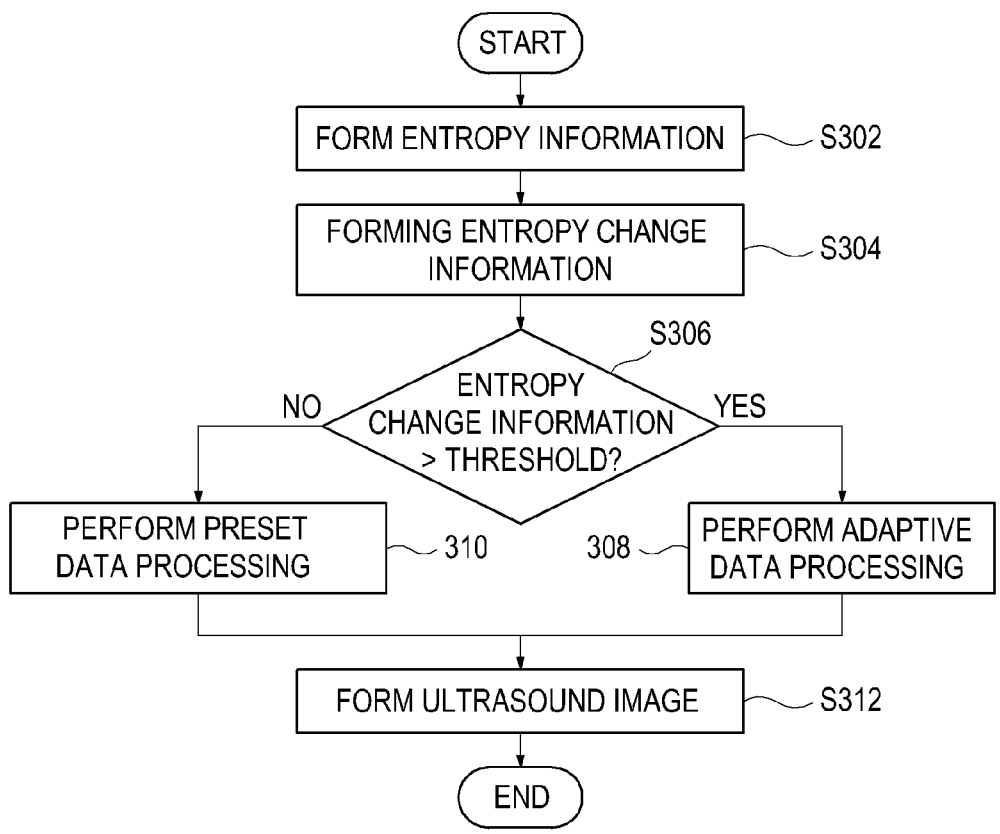
FIG. 3 is a flowchart showing a process of enhancing an image quality of an ultrasound image based on entropy information according to a first embodiment.

FIG. 3 is a flowchart showing a process of enhancing an image quality of an ultrasound image based on entropy information according to a first embodiment. Referring to FIG. 3, the processing unit 120 may be configured to form entropy information based on the ultrasound data provided from the ultrasound data acquisition unit 110, at S302. In one embodiment, the entropy information is information quantifying stochastic change degrees of corresponding information. The entropy information may include at least 1-dimensional entropy information corresponding to pixels of an ultrasound image, 2-dimensional entropy information corresponding to a two-dimensional ultrasound image and 3-dimensional entropy information corresponding to a 3-dimensional ultrasound image. The entropy information may be acquired by using various well-known methods. Thus, the detailed description thereof will be omitted herein.

In one embodiment, the processing unit 120 may be configured to form first entropy information corresponding to the B-mode images for each scan line or each frame based on the first ultrasound data. The first entropy information includes at least one of 1-dimensional entropy information and 2-dimensional entropy information as information on a stochastic change degree of intensities of the first ultrasound data. The first entropy information may be stored in the storage unit 130.

In another embodiment, the processing unit 120 may be configured to form second entropy information corresponding to the B-mode images for each scan line or each frame based on the second ultrasound data. The second entropy information includes at least one of 1-dimensional entropy information and 2-dimensional entropy information as information on a stochastic change degree of strengths of the second ultrasound data. The second entropy information may be stored in the storage unit 130. Also, the processing unit 120 may be configured to form third entropy information corresponding to the color Doppler image for each scan line or each frame based on the third ultrasound data. The third entropy information includes at least one of 1-dimensional entropy information and 2-dimensional entropy information as information on a stochastic change degree of frequency shifts or strengths of the third ultrasound data (i.e., Doppler signals). The third entropy information may be stored in the storage unit 130.

Further, in another embodiment, the processing unit 120 may be configured to form fourth entropy information corresponding to the B-mode images for each scan line or each frame based on the fourth ultrasound data. The fourth entropy information includes at least one of 1-dimensional entropy information and 2-dimensional entropy information as information on a stochastic change degree of strengths of the second ultrasound data. The fourth entropy information may be stored in the storage unit 130. Also, the processing unit 120 may be configured to form fifth entropy information corresponding to the spectral Doppler image for each scan line or each frame based on the fifth ultrasound data. The fifth entropy information includes at least one of 1-dimensional entropy information and 2-dimensional entropy information as information on a stochastic change degree of frequency shifts or strengths of the fifth ultrasound data (i.e., Doppler signals). The fifth entropy information may be stored in the storage unit 130.

In still another embodiment, the processing unit 120 may be configured to form sixth entropy information corresponding to elastic images for each scan line, each frame or each volume based on the first ultrasound data. The first entropy information includes at least one of 1-dimensional entropy information and 2-dimensional entropy information as information on a stochastic change degree of elasticity of the first ultrasound data. The six entropy information may be stored in the storage unit 130.

In further another embodiment, the processing unit 120 may be configured to form seventh entropy information corresponding to 3-dimensional ultrasound images for each scan line or each frame based on the first ultrasound data. The seven entropy information includes at least one of 1-dimensional entropy information, 2-dimensional entropy information and 3-dimensional entropy information as information on a stochastic change degree of strengthens of the first ultrasound data. The seven entropy information may be stored in the storage unit 130.

The processing unit 120 may be configured to form entropy change information indicative of temporal and spatial changes based on the entropy information, at S304. In one embodiment, the processing unit 120 may be configured to compare $i^{th}$ entropy information with $(i+1)^{th}$ entropy information to thereby form the entropy change information, wherein i is an integer greater than 0. The entropy change information may be stored in the storage unit 130.

The processing unit 120 may be further configured to compare the entropy change information with the predetermined threshold at S306. If it is determined that the entropy change information is greater than the predetermined threshold, then adaptive data processing may be performed upon the corresponding ultrasound data, at S308. On the other hand, if it is determined that the entropy change information is equal to or less than the predetermined threshold, then preset data processing may be performed upon the corresponding ultrasound data, at S310.

In one embodiment, if entropy change information between $i^{th}$ first entropy information and $(i+1)^{th}$ first entropy information is greater than the predetermined threshold, then the processing unit 120 may be operable to adaptively adjust coefficients of a filter for removing an afterimage of an ultrasound image or noise. The processing unit 120 may be operable to perform filtering upon the corresponding first ultrasound data with the adjusted filter coefficients. On the other hand, if the entropy change information is equal to or less than the predetermined threshold, then the processing unit 120 may not adjust the filter coefficients and perform filtering upon the corresponding first ultrasound data with preset filter coefficients.

In another embodiment, if entropy change information between $i^{th}$ first entropy information and $(i+1)^{th}$ first entropy information is greater than the predetermined threshold, then the processing unit 120 may be operable to adaptively adjust coefficients of a filter for enhancing an image quality of a color Doppler image. The processing unit 120 may be operable to perform filtering upon the corresponding third ultrasound data with the adjusted filter coefficients. On the other hand, if the entropy change information is equal to or less than the predetermined threshold, then the processing unit 120 may not adjust the filter coefficients for enhancing an image quality of a color Doppler image and perform filtering upon the corresponding third ultrasound data with preset filter coefficients.

In further another embodiment, if entropy change information between $i^{th}$ fourth entropy information and $(i+1)^{th}$ fourth entropy information is greater than the predetermined threshold, then the processing unit 120 may be operable to adaptively adjust coefficients of a filter for enhancing an image quality of a spectral Doppler image. The processing unit 120 may be operable to perform filtering upon the corresponding fifth ultrasound data with the adjusted filter coefficients. On the other hand, if the entropy change information is equal to or less than the predetermined threshold, then the processing unit 120 may not adjust the filter coefficients for enhancing an image quality of a spectral Doppler image and perform filtering upon the corresponding fifth ultrasound data with preset filter coefficients.

Although the above embodiments have been described that the data processing is performed upon the ultrasound data by comparing the entropy change information with the predetermined threshold, the data processing may not be limited thereto. The data processing may be performed by comparing the entropy information with a predetermined threshold.

The processing unit 120 may be configured to form an ultrasound image based on the ultrasound data with processed, at S312. Since the data processing is adaptively performed according to a rapid change of input signals by using the entropy information and/or entropy change information in processing the ultrasound data, undesirable afterimage and noise may be effectively reduced and the data processing improving a signal-to-noise ratio may be performed, as illustrated in FIG. 5.

Figure 4:
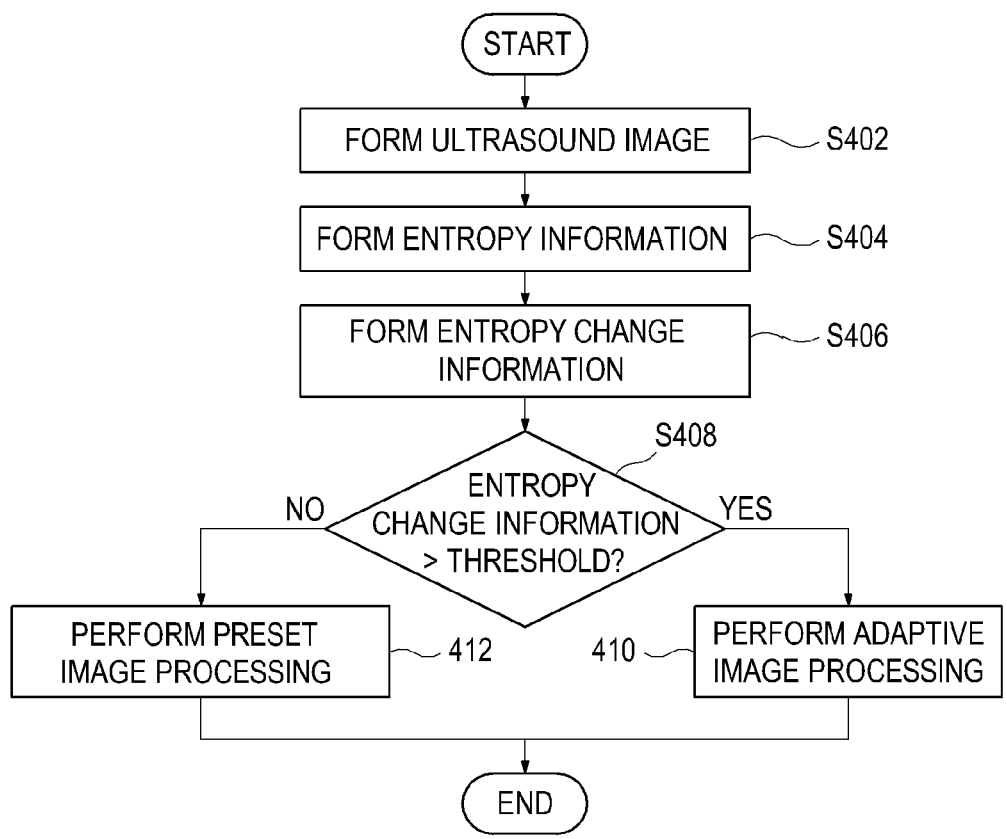
FIG. 4 is a flowchart showing a process of enhancing an image quality of an ultrasound image based on entropy information according to a second embodiment.

FIG. 4 is a flowchart showing a process of enhancing an image quality of an ultrasound image based on entropy information according to a second embodiment. Referring to FIG. 4, the processing unit 120 may be configured to form an ultrasound image by using the ultrasound data provided from the ultrasound acquisition unit 110.

In one embodiment, if the first ultrasound data are provided from the ultrasound acquisition unit 110, then the processing unit 120 may be configured to form the B-mode image by using the first ultrasound data.

In another embodiment, if the second ultrasound data are provided from the ultrasound data acquisition 110, then the processing unit 120 may be configured to form a B-mode image by using the second ultrasound data. Further, if the third ultrasound data are provided from the ultrasound data acquisition unit 110, then the processing unit 120 may be configured to form a color Doppler image by using the third ultrasound data.

In further another embodiment, if the fourth ultrasound data are provided from the ultrasound data acquisition 110, then the processing unit 120 may be configured to form a B-mode image by using the fourth ultrasound data. Further, if the fifth ultrasound data are provided from the ultrasound data acquisition unit 110, then the processing unit 120 may be configured to form a spectral Doppler image by using the fifth ultrasound data.

In further another embodiment, if the first ultrasound data are provided from the ultrasound acquisition unit 110, then the processing unit 120 may be configured to form elastic information by using the first ultrasound data and form an elastic image based on the elastic information.

In further another embodiment, if the first ultrasound data are provided from the ultrasound acquisition unit 110, then the processing unit 120 may be configured to form volume data by using the first ultrasound data and render the volume data for a 3-dimensional image.

The processing unit 120 may be further configured to form entropy information by using the ultrasound image for pixels, a region having a predetermined size or frames, at S404.

In one embodiment, the processing unit 120 may be configured to form first entropy information corresponding to the B-mode image for pixels, a region having a predetermined size or frames. The first entropy information may be stochastic change information of intensities of the first ultrasound data (i.e., ultrasound echoes reflected from the target object). The first entropy information may include at least one of 1-dimensional entropy information and 2-dimensional entropy information. The first entropy information may be stored in the storage unit 130.

In another embodiment, the processing unit 120 may be configured to form second entropy information corresponding to the B-mode image for pixels, regions having a predetermined size or frames. The second entropy information may be stochastic change information of intensities of the second ultrasound data (i.e., ultrasound echoes reflected from the target object). The second entropy information may be stored in the storage unit 130. Further, the processing unit 120 may be further configured to form third entropy information corresponding to the color Doppler image for pixels, regions having a predetermined size or frames. The third entropy information may be frequency shift or stochastic change information of the third ultrasound data (i.e., Doppler signals). The third entropy information may include at least one of 1-dimensional entropy information and 2-dimensional entropy information. The third entropy information may be stored in the storage unit 130.

In further another embodiment, the processing unit 120 may be configured to form fourth entropy information corresponding to the B-mode image for pixels, regions having a predetermined size or frames. The fourth entropy information may be stochastic change information of intensities of the second ultrasound data (i.e., ultrasound echoes reflected from the target object). The fourth entropy information may be stored in the storage unit 130. Further, the processing unit 120 may be further configured to form fifth entropy information corresponding to the spectral Doppler image for pixels, regions having a predetermined size or frames. The fifth entropy information may be frequency shift or stochastic change information of the fifth ultrasound data (i.e., Doppler signals). The fifth entropy information may include at least one of 1-dimensional entropy information and 2-dimensional entropy information. The fifth entropy information may be stored in the storage unit 130.

In further another embodiment, the processing unit 120 may be configured to form sixth entropy information corresponding to the elastic image for pixels, regions having a predetermined size or frames. The sixth entropy information may be stochastic information of elastic information. The sixth entropy information may include at least one of 1-dimensional entropy information and 2-dimensional entropy information. The sixth entropy information may be stored in the storage unit 130.

In further another embodiment, the processing unit 120 may be configured to form seventh entropy information corresponding to the 3-dimensional ultrasound image for voxels, regions having a predetermined size or frames. The seventh entropy information may be stochastic information of intensities of first ultrasound data (i.e., ultrasound echoes reflected from the target object). The seventh entropy information may include at least one of 1-dimensional entropy information, 2-dimensional entropy information and 3-dimensional entropy information. The seventh entropy information may be stored in the storage unit 130.

The processing unit 120 may be configured to form entropy change information indicative of temporal and spatial change of the entropy based on the entropy information, at S406. In one embodiment, the processing unit 120 may be configured to compare the $i^{th}$ entropy information with the $(i+1)^{th}$ entropy information to thereby form the entropy change information. The entropy change information may be stored in the storage unit 130.

The processing unit 120 may be configured to compare the entropy change information with the predetermined threshold, at S408. If the entropy change information is greater than the predetermined threshold, then the processing unit 120 may be configured to perform adaptive image processing upon the ultrasound image, at S410. On the other hand, if the entropy change information is equal to or less than the predetermined threshold, then the processing unit 120 may be configured to perform preset image processing upon the ultrasound image, at S412.

In one embodiment, if the entropy change information obtained from the $i^{th}$ first entropy information and the $(i+1)^{th}$ first entropy information is greater than the predetermined threshold, then the processing unit 120 may be configured to adaptively adjust coefficients of a filter for removing afterimage or noise of the ultrasound image and perform filtering upon the corresponding B-mode image with the adjusted filter coefficients. On the other hand, the entropy change information obtained from the $i^{th}$ first entropy information and the $(i+1)^{th}$ first entropy information is equal to or less than the predetermined threshold, then the processing unit 120 may not adjust filter coefficients and perform filtering upon the corresponding B-mode image with preset filter coefficients.

In another embodiment, if the entropy change information obtained from the $i^{th}$ second entropy information and the $(i+1)^{th}$ second entropy information is greater than the predetermined threshold, then the processing unit 120 may be configured to adaptively adjust coefficients of a filter for enhancing an image quality of the color Doppler image and perform filtering upon the corresponding color Doppler image with the adjusted filter coefficients. On the other hand, the entropy change information obtained from the $i^{th}$ second entropy information and the $(i+1)^{th}$ second entropy information is equal to or less than the predetermined threshold, then the processing unit 120 may not adjust filter coefficients and perform filtering upon the corresponding color Doppler image with preset filter coefficients.

In further another embodiment, if the entropy change information obtained from the $i^{th}$ fourth entropy information and the $(i+1)^{th}$ fourth entropy information is greater than the predetermined threshold, then the processing unit 120 may be configured to adaptively adjust coefficients of a filter for enhancing an image quality of the spectral Doppler image and perform filtering upon the corresponding color Doppler image with the adjusted filter coefficients. On the other hand, the entropy change information obtained from the $i^{th}$ fourth entropy information and the $(i+1)^{th}$ fourth entropy information is equal to or less than the predetermined threshold, then the processing unit 120 may not adjust filter coefficients and perform filtering upon the corresponding spectral Doppler image with preset filter coefficients.

Although the above embodiments have been described that the image processing is adaptively performed by comparing the entropy change information with the predetermined threshold, the image processing may not be limited thereto. The image processing of the ultrasound image may be adaptively performed by comparing the entropy information with a predetermined threshold.

Therefore, since the image processing is adaptively performed according to a rapid change of input signals by using the entropy information and/or entropy change information in processing the ultrasound image, undesirable afterimage and noise may be effectively reduced and the image processing improving a signal-to-noise ratio may be performed, Referring to FIG. 1, the storage unit 130, which is coupled to the ultrasound data acquisition unit 110 via the processing unit 120, is configured to store the ultrasound data acquired in the ultrasound data acquisition unit 120. Also, the storage unit 130 may be configured to store the entropy information.

The display unit 140 may display the ultrasound images, which have been formed in the processing unit 120. The display unit 140 may further display the entropy information or the entropy change information, which have been formed in the processing unit 120. The display unit 140 may include at least one of a cathode ray tube (CRT) display, a liquid crystal display (LCD), an organic light emitting diode (OLED) display and the like.

In anther embodiment, the entropy information may be formed based on the ultrasound data and image processing for enhancing an image quality of an ultrasound image may be formed based on the entropy information. Further, gain of a Doppler sound may be adjusted by using the entropy information.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound data acquisition unit including an ultrasound probe configured to perform a transmit/receive operation including transmitting ultrasound signals to a target object and receiving rapidly changing ultrasound echoes reflected from the target object to thereby acquire multiple ultrasound data; and
a processor configured to:
form entropy information indicating a stochastic change degree of the multiple ultrasound data in an order in which the ultrasound data associated with the rapidly changing ultrasound echoes are acquired,
form entropy change information indicating a difference between an i-th entropy information of the formed entropy information associated with the rapidly changing ultrasound echoes and an (i+1)-th entropy information of the formed entropy information associated with the rapidly changing ultrasound echoes,
compare the entropy change information with a threshold in entropy change information,
when the entropy change information is greater than the threshold in entropy change information, adaptively adjust coefficients of a filter for removing afterimage or removing noise in multiple ultrasound images and perform filtering for removing afterimage or removing noise in the multiple ultrasound images upon the multiple ultrasound data with the filter having the adjusted coefficients,
when the entropy change information is equal to or less than the threshold in entropy change information, perform filtering for removing afterimage or removing noise in the multiple ultrasound images upon the multiple ultrasound data with the filter having preset coefficients, without adjusting coefficients of the filter, and
the processor being further configured to form the multiple ultrasound images based on the multiple ultrasound data with the filtering performed.

2. The ultrasound system of claim 1, wherein the multiple ultrasound images include a color Doppler image, the filter is further for enhancing an image quality of the color Doppler image, and the processor is further configured to perform filtering for enhancing the image quality of the color Doppler image upon the multiple ultrasound data with the filter and form the color Doppler image based on the multiple ultrasound data with the filtering performed.

3. The ultrasound system of claim 1, wherein the multiple ultrasound images include a spectral Doppler image, the filter is further for enhancing an image quality of the spectral Doppler image, and the processor is further configured to perform filtering for enhancing the image quality of the spectral Doppler image upon the multiple ultrasound data with the filter and form the spectral Doppler image based on the multiple ultrasound data with the filtering preformed.

4. An ultrasound system, comprising:
an ultrasound data acquisition unit including an ultrasound probe configured to perform a transmit/receive operation including transmitting ultrasound signals to a target object and receiving rapidly changing ultrasound echoes reflected from the target object to thereby acquire multiple ultrasound data; and
a processor configured to:
form entropy information indicating a stochastic change degree of the multiple ultrasound data in an order in which the ultrasound data associated with the rapidly changing ultrasound echoes are acquired,
form entropy change information indicating a difference between an i-th entropy information of the formed entropy information associated with the rapidly changing ultrasound echoes and an (i+1)-th entropy information of the formed entropy information associated with the rapidly changing ultrasound echoes, and
form multiple ultrasound images based on the multiple ultrasound data, the processor being further configured to:

compare the entropy change information with a threshold in entropy change information, when the entropy change information is greater than the threshold in entropy change information, adaptively adjust coefficients of a filter for removing afterimage or noise of the multiple ultrasound images and perform filtering for removing afterimage or removing noise in the multiple ultrasound images upon the multiple ultrasound images with the filter having the adjusted coefficients, and when the entropy change information is equal to or less than the threshold in entropy change information, perform filtering for removing afterimage or removing noise in the multiple ultrasound images upon the multiple ultrasound images with the filter having preset coefficients, without adjusting coefficients of the filter.

5. A method of enhancing an image quality of ultrasound images, comprising:
   a) performing a transmit/receive operation including transmitting ultrasound signals to a target object and receiving rapidly changing ultrasound echoes reflected from the target object to thereby acquire multiple ultrasound data;
   b) forming entropy information indicating stochastic change degree of the multiple ultrasound data in an order in which the ultrasound data associated with the rapidly changing ultrasound echoes are acquired;
   c) forming entropy change information indicating a difference between an i-th entropy information of the formed entropy information associated with the rapidly changing ultrasound echoes and an (i+1)-th entropy information of the formed entropy information associated with the rapidly changing ultrasound echoes;
   d) comparing the entropy change information with a threshold in entropy change information;
   e) when the entropy change information is greater than the threshold in entropy change information, adaptively adjusting coefficients of a filter for removing afterimage or removing noise in multiple ultrasound images and performing filtering upon the multiple ultrasound data with the filter having the adjusted coefficients, and
   when the entropy change information is equal to or less than the threshold in entropy change information, performing filtering for removing afterimage or removing noise in the multiple ultrasound images upon the multiple ultrasound data with the filter having preset coefficients, without adjusting coefficients of the filter; and
   f) forming the multiple ultrasound images based on the multiple ultrasound data with the filtering performed.

6. The method of claim 5,
wherein the step f) includes:
performing filtering upon the multiple ultrasound images.

* * * * *